United States Patent [19]

Stumm

[11] Patent Number: 4,562,349
[45] Date of Patent: Dec. 31, 1985

[54] METHOD AND APPARATUS FOR SCANNING THE SURFACE OF AN OBJECT

[75] Inventor: Wolfgang Stumm, Reutlingen, Fed. Rep. of Germany

[73] Assignee: Institut Dr. Friedrich Förster Prüfgerätebau GmbH & Co KG, Reutlingen, Fed. Rep. of Germany

[21] Appl. No.: 516,986

[22] Filed: Jul. 25, 1983

[30] Foreign Application Priority Data

Jun. 7, 1983 [DE] Fed. Rep. of Germany ....... 3230368

[51] Int. Cl.⁴ ............................................. H01J 5/16
[52] U.S. Cl. .................................. 250/234; 358/199; 358/208
[58] Field of Search ...................... 250/224, 234–236, 250/216; 358/199, 208

[56] References Cited

U.S. PATENT DOCUMENTS

| | | | |
|---|---|---|---|
| 2,855,521 | 10/1958 | Blackstone | 250/234 |
| 3,564,266 | 4/1968 | Klotz, Jr. | 250/234 |
| 4,352,984 | 10/1982 | Ohara | 250/234 |
| 4,455,485 | 6/1984 | Hosaka et al. | 250/234 |

*Primary Examiner*—David C. Nelms
*Assistant Examiner*—J. Jon Brophy
*Attorney, Agent, or Firm*—George J. Netter

[57] ABSTRACT

Method and apparatus for scanning an object with a probe in which scanning lines for the forward and backward motions run parallel to each other and their mutual spacing from each other remains constant. In one form, the object transportation speed Vt is set relative to the speed Va of the forward and backward motions in such a way that $Vt/Va = \tangent \alpha = $constant where $\alpha$ is of the angle between the line of reciprocating movement and a normal to the transportation direction. According to another feature, the angle may be controlled by Vt such that parallelism of the scanning lines is maintained.

6 Claims, 5 Drawing Figures

METHOD AND APPARATUS FOR SCANNING THE SURFACE OF AN OBJECT

The present invention relates to a method for scanning the surface of an object by means of a scanning head, and to apparatus for execution of this method.

FIELD OF THE INVENTION

There are many situations in which it is desirable to scan the surface of an object with detection means of some kind. For example, a specific form of advantageous utilization of the described method is to scan completely the surface of semifinished material (e.g., an iron slab or billet) by means of non-destructive testing probes (e.g. eddy current probes) for defects and to locate their position and size. A sine-shaped scanning motion for that purpose is described in German patent publication No. DE-OS 1773501. The utilization of filters for interference suppression has the result that uniform speed of the forward and backward scanning motion was sought and even achieved within certain limits (German patent publication No. DE-OS 2745159) with the resulting scanning tracks exhibiting a generally trapezoidal shape.

If one succeeds in keeping the time for reversing the motion negligibly small compared to the duration of the scanning period, a nearly triangular shape can be achieved. This meets all requirements, if for a given sufficiently large scanning speed even the smallest defect to be detected is covered several times by the scanning head. If, however, for a limited speed of scanning in a short time as possible a defect having a certain length extending in the direction of transportation is to be detected accurately and reliably, the scanning lines must be arranged parallel to each other at a spacing from each other that is smaller than the length of the defect. The desirability for parallel scanning lines may also result, if for a triangular scanning track, instead of point scanning, the scanning probe has a significant width and if no area of the surface is to be scanned twice.

SUMMARY OF THE DISCLOSURE

In accordance with the desired invention there is provided a simple method and apparatus for carrying out the method in which scanning lines for the forward and backward motions run parallel to each other and that their mutual spacing from each other remain constant. It is true that, for a triangular scanning track, the scanning lines are parallel, if the backward motion is not utilized. In contrast, however, the described invention delivers and appreciable gain of time: for completing scanning, only half of the time is necessary, as both forward and backward motions are utilized.

According to an alternate aspect of the invention, in case of varying transportation speed Vt, the speed Va of the forward and backward motions is controlled by Vt in such a way that $Vt/Va = \text{tangent } \alpha = \text{constant}$. For the same case, according to another feature of the invention, the angle $\alpha$ may be controlled by Vt such that parallelism of the scanning lines is maintained.

DESCRIPTION OF PREFERRED EMBODIMENTS

Figure 1A:
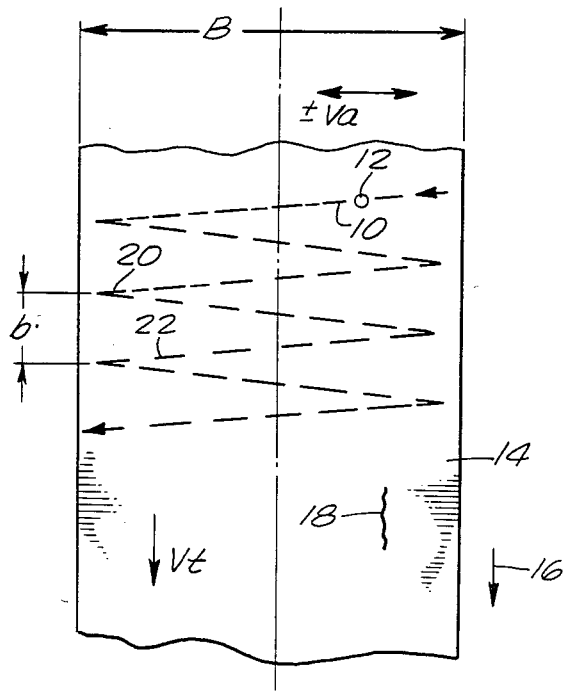
FIGS. 1a and 1b depict scanning tracks of prior known systems.

FIG. 1a shows the shape of a scanning track 10 of effectively a point probe 12 on an iron slab 14. The scanning track 10 results from the iron slab 14 moving in the direction of the arrow 16 at a speed Vt, whereas the probe 12 is moving to and fro (transversely of 14) with the speed ±Va between two final points. Reversing of the motion of probe 12 at the final points from +Va to −Va must take place in negligibly short time. A defect 18 the length of which exceeds slightly the distance b between the scanning lines 20 and 22 is only detected accurately and reliably when the probe 12 has performed a full scanning cycle with forward and backward motion. The time T for a cycle is $T = B \cdot Va = b \cdot Vt$, B being the width of the iron slab or billet.

Figure 1B:
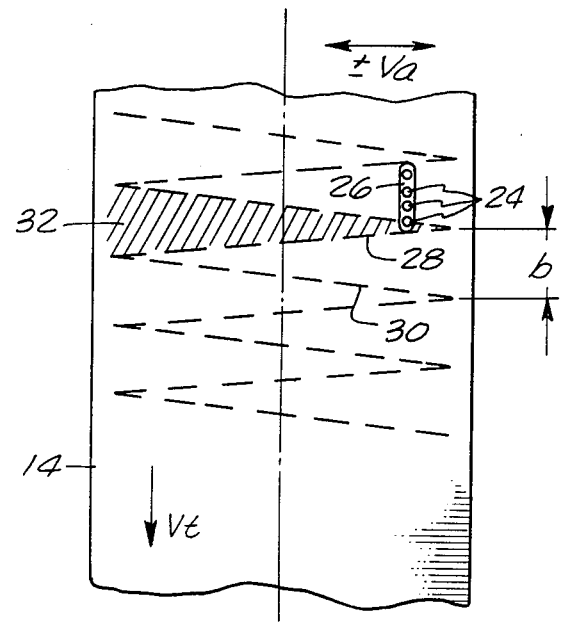

In FIG. 1b, the single probe 12 is replaced by several individual probes 24 in a probe arrangement 26, the length of which corresponds approximately to the distance b between the two scanning lines 28 and 30 and which is effective to sense all defects covered by the extended length of the probe arrangement 26. It turns out that for each cycle of the probe arrangement 26, a wedge 32 is scanned, having been scanned in the previous cycle already, and that, thus, the whole area is scanned twice. Beside the fact that such a double scanning could be, per se, not desirable (e.g., in case of a processing procedure instead of a scanning for defects) in any case loss of time involved is not necessary. In the total time 2T for a scanning cycle, the doubled area may be scanned, if one succeeds in achieving a parallel course for the scanning tracks in the to and fro motion.

Figure 2:
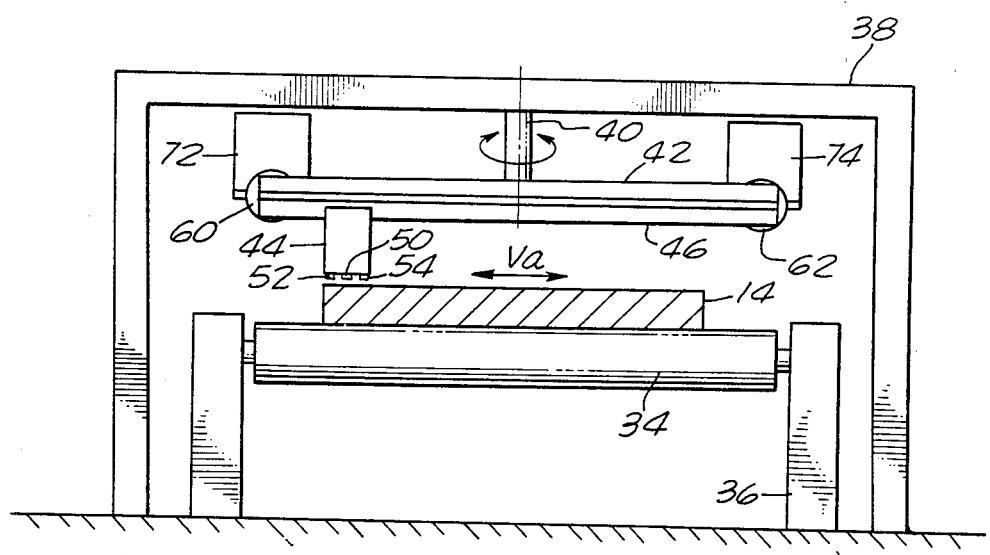
FIG. 2 shows an elevational view of apparatus according to the invention.
Figure 3:
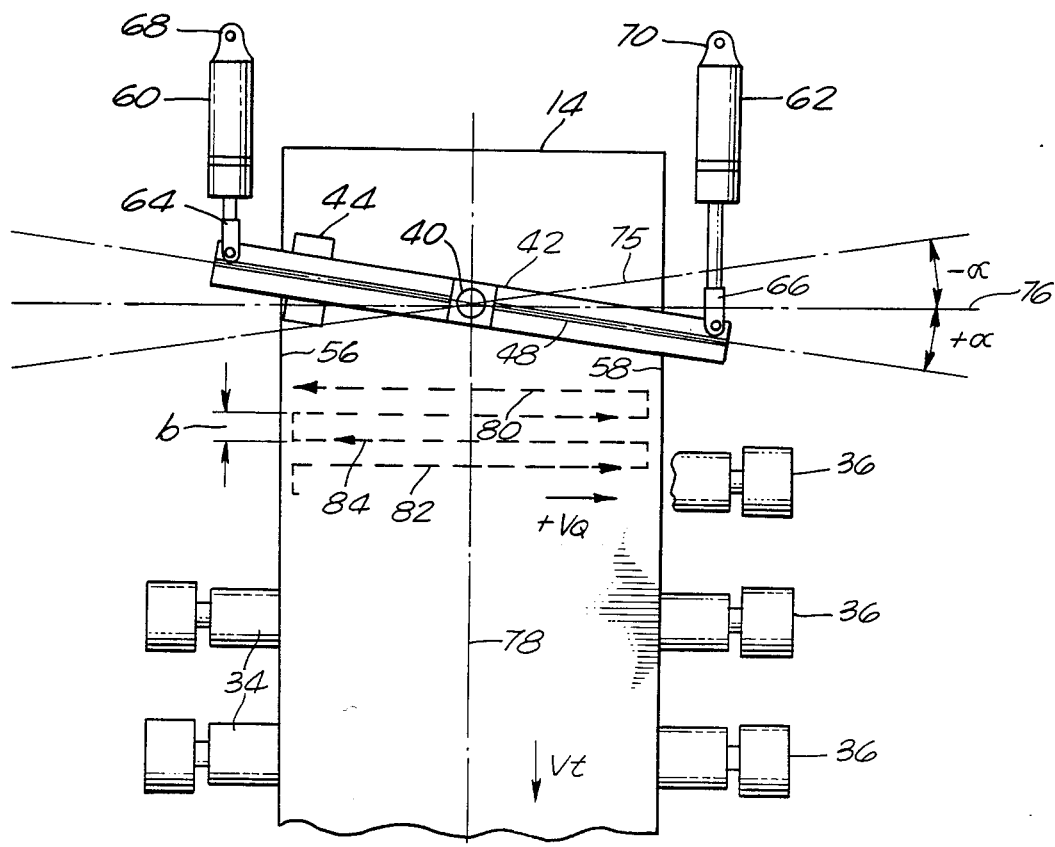
FIG. 3 shows a top plan view of the apparatus of FIG. 2.

FIGS. 2 and 3 show end elevational and top plan views, respectively, of an apparatus, in which the parallel course of the forward and backward motions of scanning tracks is achieved. The iron slab or billet 14 rests on roller 34 of a table conveyor 36 and is transported by it at the speed Vt under a girder 38. In the center of the conveyor 36, a support arm 42 is pivotable about an axle 40 carried by the girder 38. A scanning head 44 rides on guide rail 46 attached to the support arm 42, this rail allowing motions of the scanning head along a line 48. The scanning head 44 is provided with a drive system containing a driving motor, this system not being represented in detail for simplicity reasons, and serving to drive the scanning head in both directions along the line 48 with a corresponding speed ±Va. Alternatively, a drive system mounted on the support arm 42 may be provided causing the scanning head 44 to move at the speed ±Va.

The scanning head 44 contains in the present example an eddy current probe 50 as scanning device, this probe being in either sliding contact with or spaced from the surface of the iron slab 14, in order to scan it completely. Furthermore, two material sensors 52, 54 are incorporated in the scanning head delivering an electrical signal when they reach the edge 56 or 58, respectively, of the iron slab 14.

Two hydraulic cylinders 60, 62 act via their yokes 64, 66 upon the ends of the support arm 42, the other ends thereof being borne by ears 68, 70 from supports 72, 74 mounted on the girder 38. The hydraulic cylinders may be stroke-pressure cylinders. In case they are arranged, as in the present example, on the same side in the direction of movement of 14, they are actuated alternately in stroke or in pressure direction, respectively. In the same way, of course, one of the cylinders can be arranged on the opposite side in transporation direction 78. In this case, both cylinders would have to be actuated simultaneously each in stroke or in pressure direction, respectively. The task of the two cylinders is the rapid repositioning of the support arm 42 and, thus, of the scanning head 44 along the course 48 at the angle $-\alpha$ and back at the angle $+\alpha$ in relation to the line 76 normal to the direction of transportation along line 78. To change the value of the angle $\alpha$, requires adjustment of the travel of the hydraulic cylinders 60, 62 and the position of the ears 68, 70.

The meander-shaped scanning track 80 results as follows: during the transportation of the iron slab 14 with the speed Vt, the scanning head 44 moves, guided by the guide rail 46 adjusted to the angle $+\alpha$, along the line 48 with the speed $+Va$ from left to right. When the condition $\tan\alpha = Vt/Va$ is met, a scanning line on the iron slab corresponding to line 82 is formed. At the end of this line 82, as reaction to a signal of the sensor 54, the transverse motion of the scanning head 44 is reversed to the opposite direction. Simultaneously, both hydraulic cylinders 60, 62 are actuated and reverse at a high speed the guide rail 46 to the angle $-\alpha$, such that the scanning head 44 now moves along the line 75 from right to left with the speed $-Va$ resulting in a new scanning line 84 on the iron slab. At its end, the sensor 52 reverses the motion of the scanning head 44 once again and the repositioning of the guide rail 46 by actuation of the hydraulic cylinders 60, 62 are effected. All scanning lines 82, 84 and so forth run parallel to each other and normally to the direction of transportation of the iron slab 14. Furthermore, the scanning lines 82, 84 are spaced equal distances from each other, provided that the center or rotation 40 is placed in the center of the scanning track 80.

By known control apparatus, the speed Va can be brought to the value necessary for fulfilling the condition $\tan\alpha = Vt/Va$. In that case, a speed sensor produces a signal depending on the speed Vt of the iron slab. Such a procedure has the advantage that even on varying Vt, the parallelism and the equidistance of the scanning lines is maintained. Within a certain limited range, it is even possible that the angle $\alpha$ is controlled by the speed Vt in such a way that the parallelism and the equidistance of the scanning lines are maintained.

Figure 4:
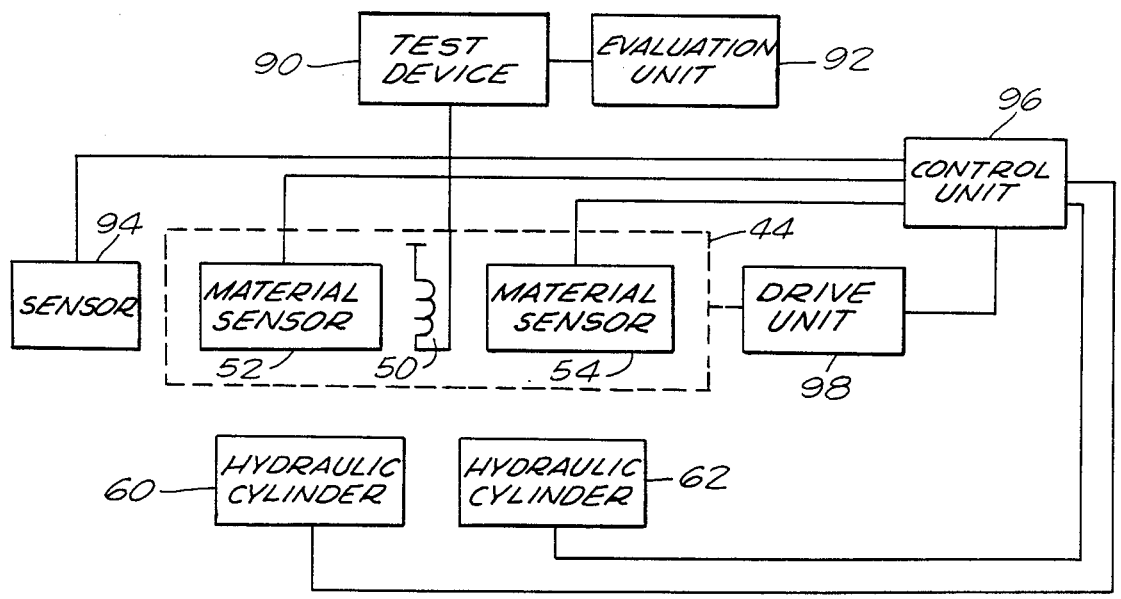
FIG. 4 depicts a circuit diagram of the described apparatus.

FIG. 4 shows a simplified circuit diagram of apparatus for execution of the method according to the invention. The eddy current probe 50 is connected to an eddy current test device 90, which, in turn, is connected to a corresponding evaluation unit 92. Probe 50 is, together with the material sensors 52, 54, integrated in a scanning head 44. A speed sensor 94 produces a signal depending on the speed Vt of the iron slab 14. The outputs of the sensors 52, 54, 94 are connected to the inputs of a control and arithmetic unit 96. Depending on values of the signals of the sensors 52, 54, 94, control signals for the hydraulic cylinders 60 and 62 and for a drive unit 98 are provided for driving the forward and backward motions of the scanning head 44 with the speed $\pm Va$.

I claim:

1. In a method of scanning the surface of an object by a head, said object and head moving relative to each other along a straight line at a velocity Vt, said head further oscillating linearly at a uniform velocity of Va along a direction having a vertical component to the straight line direction of relative movement, the improvement comprising:
    adjusting the angle of the linear oscillating direction to form an angle $\alpha$ with a line at right angles to the straight line direction of relative movement between the object and scanning head were $\alpha = \arctan Vt/Va$.

2. A method as in claim 1, in which $Vt/Va = \tan\alpha =$ constant.

3. A method as in claim 1, in which Vt is so chosen that consecutive straight lines of relative movement are equidistant from one another and parallel.

4. In apparatus for scanning the surface of an object by a scanning head in which means are provided for establishing first relative movement between the object and scanning head along a straight path at a velocity Vt, means for reciprocating the scanning head along a second path generally transversely of the first straight path at a velocity Va, said reciprocating means including guide means having a track along which the scanning head is reciprocatingly driven, the improvement comprising:
    means pivotally mounting the guide means for movement in a plane parallel to a surface of the object; and
    means selectively adjustable to position the track on the guide means at a predetermined angle to a line at ninety degrees to the first straight line path.

5. Apparatus as in claim 4, in which the pivot point is located at the midpoint between the limits of reciprocating movement.

6. Apparatus as in claim 4, in which the selectively adjustable positioning means includes hydraulic means interconnected with the guide means to pivot said guide means.

* * * * *

UNITED STATES PATENT AND TRADEMARK OFFICE
CERTIFICATE OF CORRECTION

PATENT NO. : 4,562,349

DATED : December 31, 1985

INVENTOR(S) : Wolfgang Stumm

It is certified that error appears in the above-identified patent and that said Letters Patent is hereby corrected as shown below:

Page 1, the Foreign Application Priority Date should be August 14, 1982.

Signed and Sealed this

Twenty-seventh Day of May 1986

[SEAL]

Attest:

DONALD J. QUIGG

Attesting Officer

Commissioner of Patents and Trademarks